United States Patent [19]

Jones et al.

[11] 4,057,642

[45] Nov. 8, 1977

[54] ACYL CYANOGUANIDINES

[75] Inventors: Howard Jones, Holmedl; Tsung-Ying Shen, Westfield, both of N.J.

[73] Assignee: Merck & Co., Inc., Rahway, N.J.

[21] Appl. No.: 618,107

[22] Filed: Sept. 30, 1975

[51] Int. Cl.$^2$ .............. A61K 31/165; A61K 31/275; C07C 103/20
[52] U.S. Cl. .................... 424/304; 260/558 S; 424/324
[58] Field of Search ............ 260/551 C, 558 S; 424/304, 324

[56] References Cited

U.S. PATENT DOCUMENTS

| 2,315,765 | 4/1943 | Bindler | 260/551 C |
| 2,407,161 | 9/1946 | Kaiser et al. | 260/551 C |

*Primary Examiner*—Frederick E. Waddell
*Attorney, Agent, or Firm*—Raymond M. Speer; Harry E. Westlake, Jr.; Frank M. Mahon

[57] ABSTRACT

Certain novel acyl cyanoguanidines, their preparation, pharmaceutical compositions and novel methods of treating inflammation and autoimmune diseases such as rheumatoid arthritis are disclosed.

5 Claims, No Drawings

ACYL CYANOGUANIDINES

BACKGROUND OF THE INVENTION

In spite of the extensive antiinflammatory research in the past two decades there is still an obvious need for an effective and well-tolerated agent for the treatment of rheumatoid arthritis. Conventional antiinflammatory-analgesic-antipyretic agents, such as aspirin, and many experimental new drugs under clinical evaluation, are mostly effective in providing symptomatic relief of the acute syndrome only. As a consequence, the antirheumatic actions of two other remedies, gold and particularly D-penicillamine, have received renewed interest in the past few years. The clinical efficacy of both drugs has been confirmed by well-controlled multi-center clinical studies. Impressed by these findings, a growing population of rheumatologists have expressed the opinion that compounds possessing properties similar to D-penicillamine should be a valuable contribution to medicine in this important field. Thus it is an important discovery that acyl cyanoguanidines possess immunological properties similar to that of D-penicillamine, being of value in the treatment of rheumatoid arthritis and related inflammatory disorders, as well as antiinflammatory properties.

DETAILED DESCRIPTION OF THE INVENTION

This invention relates to a novel class of acyl cyanoguanidines useful for treating inflammation and auto-immune diseases, such as rheumatoid arthritis. The novel acyl cyanoguanidines of the invention have the following structural formula:

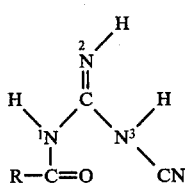

I wherein
R is $C_{1-5}$alkylthiophenyl, $C_{1-5}$alkylsulfinylphenyl or $C_{1-5}$alkylsulfonylphenyl. The substituent groups may be in the ortho, meta or para positions of the aromatic ring.

In a preferred embodiment, R is methylthiophenyl, methylsulfinylphenyl or methylsulfonylphenyl.

In a more preferred embodiment, R is methylthiophenyl.

The following novel compounds are representative of this invention:
1-(2'-methylthiobenzoyl)-3-cyanoguanidine,
1-(2'-methylsulfinylbenzoyl)-3-cyanoguanidine,
1-(2'-methylsulfonylbenzoyl)-3-cyanoguanidine,
1-(3'-methylthiobenzoyl)-3-cyanoguanidine,
1-(3'-methylsulfinylbenzoyl)-3-cyanoguanidine,
1-(3'-methylsulfonylbenzoyl)-3-cyanoguanidine,
1-(4'-ethylthiobenzoyl-3-cyanoguanidine,
1-(2'-ethylsulfinylbenzoyl)-3-cyanoguanidine,
1-(2'-ethylsulfonylbenzoyl)-3-cyanoguanidine.

Another aspect of this invention relates to the novel pharmaceutical compositions for treating inflammation and autoimmune diseases such as rheumatoid arthritis comprising a non-toxic pharmaceutically acceptable carrier and a compound of formula IV:

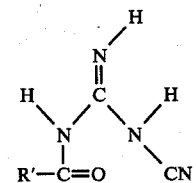

IV wherein
R' is $C_{1-5}$alkoxyphenyl, $C_{1-5}$alkylthiophenyl, $C_{1-5}$alkylsulfinylphenyl or $C_{1-5}$alkylsulfonylphenyl. In a preferred embodiment R' is methoxyphenyl or methylthiophenyl.

The non-toxic pharmaceutical carrier may be, for example, either a solid or a liquid. Exemplary of solid carriers are lactose, corn starch, gelatin, talc sterotix, stearic acid, magnesium stearate, terra alba sucrose, agar, pectin and acacia. Exemplary of liquid carriers are peanut oil, olive oil, seasame oil and water. Similarly the carrier or diluent may include a time delay material such as glyceryl monostearate or glyceryl distearate, alone, or with a wax.

The treatment of inflammation and autoimmune diseases, such as rheumatoid arthritis, in accordance with the method of the present invention is accomplished by orally, rectally, parenterally or topically administering to patients the compounds of formula IV, supra, or mixtures thereof in a non-toxic pharmaceutically acceptable carrier.

Several pharmaceutical forms of the therapeutically useful compositions may be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, a liquid solution, a liquid emulsion or a liquid suspension. Suppositories may be prepared in the conventional manner by mixing the compounds of this invention with a suitable non-irritating excipient which is solid at room temperature. Exemplary of excipients are cocoa butter and polyethylene glycol. Gels, lotions and aerosol sprays for topical application may be prepared in conventional manners.

The active compounds of formula IV, supra, are administered in a therapeutically effective amount sufficient to treat inflammation and autoimmune diseases such as rheumatoid arthritis. The treatment of rheumatoid arthritis is one condition where the treatment of inflammation and the autoimmune disorder will improve the condition, and accordingly the amount of active compound necessary to treat inflammation and the autoimmune disorder is the amount required to treat the rheumatoid arthritis. Advantageously, the active compounds will be administered, alone or in a pharmaceutical composition in an amount of from about 1.0 mg to 100 mg per kg body weight per day (50 mg to 5.0 g per patient per day of the active compound, preferably from about 1.5 mg to 15 mg per kilogram body weight per day. The daily dosage may be given in either single or multiple dosages.

The method of treatment of this invention comprises administering to a patient (animal or human) the compound as previously described admixed with a non-toxic pharmaceutical carrier such as exemplified above. It should be understood that although preferred dosage ranges are given, the dose level for any particular patient depends upon the activity of the specific compound employed. Also many other factors that modify the actions of drugs will be taken into account by those skilled in the art in the therapeutic use of medicinal agents, particularly those described above; for example, body weight, sex, diet, time of administration, route of administration, rate of excretion, drug combination, reaction sensitivities and severity of the particular disease.

Another aspect of this invention is the process for preparing the novel compounds of formula I, supra, wherein R is as defined above, by reacting a compound of the formula:

            II wherein X is halo, such as chloro or bromo, with a compound of the formula:

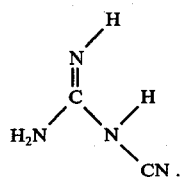            III

The compound of formula III, supra, also known as dicyanodiamide or cyanoguanidine, exists in several tautomeric forms. Reactants II and III are present in approximately equal molar amounts.

The reaction may be carried out in a suitable solvent. The solvent may be a ketone, such as acetone or methyl ethyl ketone, an ether, such as diethyl ether, a cyclic ether, such as tetrahydrofuran (THF) or dioxan, an amide, such as dimethylformamide (DMF), dimethylacetamide (DMA) or hexamethylphosphoramide (HMPA), a hydrocarbon such as benzene, toluene or xylene, a pyridine or a tri($C_{1-3}$alkyl)amine.

The reaction may also be carried out in the presence of a base in an equal molar or greater amount to remove the hydrogen halide formed by the reaction. If the base is a liquid, such as a pyridine or a tri($C_{1-3}$alkyl)-amine, it may also serve as the solvent. Other bases which may be used are the alkali metal hydroxides, amides, carbonates or bicarbonates and the alkaline earth hydroxides, oxides, carbonates and bicarbonates. Examples of suitable bases are sodium hydroxide, potassium hydroxide, calcium carbonate, pyridine and triethylamine.

The reaction temperature is not critical and generally the reaction is carried out at a temperature of from about $-20°$ C to $+30°$ C, preferably at ambient temperatures. The time of reaction is not critical and generally the reaction is carried out until it is essentially complete. The pressure is not critical and generally the reaction is carried out at atmospheric pressure in an open system. The product of the reaction, a compound of formula I, may be recovered in the conventional manner, such as by extraction or crystallation.

The starting materials employed in the foregoing processes have been described in the literature and many are commercially available, except as described below. For example, the $C_{1-5}$alkylthiobenzoic acids may be produced from known $C_{1-5}$alkylthiobenzenes by aromatic halogenation, using a halogenating agent, such as bromine or chlorine and an aromatic ring halogenation catalyst, such as ferric magnesium compound is also known as a Grignard compound) in solution into which gaseous carbon dioxide is bubbled. The free acid may be liberated by acidification of the solution with an acid such as hydrochloric acid or sulfuric acid. The thio group may be oxidized to the sulfinyl group or the sulfonyl group by reaction with an oxidizing agent such as a peracid, potassium permanganate or hydrogen peroxide. The carboxylic acids may be converted to the corresponding acid halids by reaction with a halogenating agent such as phosphorous trihalide, phosphorous pentahalide, carbonyl halide and thionyl halide. Examples of suitable halogenating agents are phosphorous trichloride, phosgene and thionyl chloride.

The following examples are given to illustrate the invention and are not intended to limit it in any manner. All parts are given in parts by weight unless otherwise expressed.

EXAMPLE 1

1-(4'-Methylthiobenzoyl)-3-cyanoguanidine

A. 4-Methylthiobenzoyl chloride

4-Methylthiobenzoic acid, 16.8 g (0.1 mole) is refluxed for 30 minutes in 50 ml of thionyl chloride ($SOCl_2$) and 1 drop of dimethylformamide (DMF). The thionyl chloride is removed under vacuum and azeotroped with 50 ml of benzene to give 4-methylthiobenzoyl chloride as an oil.

Similarly, when an equivalent amount of 2-methoxybenzoic acid (also known as o-anisic acid), 3-methoxybenzoic acid (also known as m-anisic acid), 4-methoxybenzoic acid (also known as p-anisic acid), 4-methylsulfinylbenzoic acid or 4-methylsulfonylbenzoic acid is substituted for the 4-methylthiobenzoic acid in the above example, there is obtained 2-methoxybenzoyl chloride, 3-methoxybenzoyl chloride 4-methoxybenzoyl chloride, 4-methylsulfinylbenzoyl chloride or 4-methylsulfonylbenzoyl chloride.

B. 1-(4'Methylthiobenzoyl)-3-cyanoguanidine

Potassium hydroxide, 13.02 g (0.2 mole) is dissolved in 40 ml of water and 10.51 g (0.125 mole) of dicyanodiamide is added, followed by the addition of 50 ml of acetone. The mixture is cooled to 0° C and the 4-methylthiobenzoyl chloride from Step 1A, above, is added dropwise. The mixture is stirred at 0° C for 1 hour and placed in the refrigerator overnight. The mixture is poured into 500 ml of water and the water is then acidified with an excess of acetic acid. The product forms a precipitate which is filtered, washed with water followed by ether and air dried to give 12.1 g of 1-(4'-methylthiobenzoyl)-3-cyanoguanidine, m.p. 314° C dec.

Similarly, when an equivalent amount of 2-methoxybenzoyl chloride, 3-methoxybenzoyl chloride, 4-methoxybenzoyl chloride, 4-methylsulfinylbenzoyl chloride or 4-methylsulfonylbenzoyl chloride is substituted for the 4-methylthiobenzoyl chloride in the above example, there is obtained 1-(2'-methoxybenzoyl)-3-cyanoguanidine, m.p. 193°–194° C, 1-(3'-methoxybenzoyl)-3-cyanoguanidine, m.p. greater than 330° C, 1-(4'-methoxybenzoyl)-3-cyanoguanidine, m.p. 280° C dec. g 1-(4'-methylsulfinylbenzoyl)-3-cyanoguanidine or 1-(4'-methylsulfonylbenzoyl)-3-cyanoguanidine.

EXAMPLE 2

A mixture of 250 parts of 1-(4'-methylthiobenzoyl)-3-cyanoguanidine and 25 parts of lactose is granulated with suitable water, and to this is added 100 parts of maize starch. The mass is passed through a 16 mesh screen. The granules are dried at a temperature below 60° C. The dry granules are passed through a 16 mesh screen, and mixed with 3.8 parts of magnesium stearate. They are then compressed into tablets suitable for oral administration.

Similarly, an equivalent amount of 1-(2'-methoxybenzoyl)-3-cyanoguanidine, 1-(3-methoxybenzoyl-3-cyanoguanidine, 1-(4'-methoxybenzoyl)-3-cyanoguanidine, 1-(4'-methylsulfinylbenzoyl)-3-cyanoguanidine or 1-(4'-methylsulfonylbenzoyl)-3-cyanoguanidine may be substituted for the 1-(4'-methylthiobenzoyl)-3-cyanoguanidine in the above pharmaceutical composition.

EXAMPLE 3

A mixture of 50 parts of 1-(4'-methylthiobenzoyl)-3-cyanoguanidine, 3 parts of the calcium salt of lignin sulphonic acid, and 237 parts of water is ball-milled until the size of substantially all of the particles of the acid is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

Similarly, an equivalent amount of 1-(2'-methoxybenzoyl)-3-cyanoguanidine, 1-(3'-methoxybenzoyl)-3-cyanoguanidine, 1-(4'-methoxybenzoyl)-3-cyanoguanidine, 1-(4'-methylsulfinylbenzoyl)-3-cyanoguanidne or 1-(4'-methylsulbenzoyl)-3-cyanoguanidine may be substituted for the 1-(4'methylthiobenzoyl)-3-cyanoguanidine in the above pharmaceutical composition.

EXAMPLE 4

A mixture of 250 parts of 1-(4'-methylthiobenzoyl)-3-cyanoguanidine, 200 parts of maize starch and 30 parts of alginic acid is mixed with a sufficient quantity of 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

Similarly, an equivalent amount of 1-(2'-methoxybenzoyl)-3-cyanoguanidine, 1-(3'-methoxybenzoyl)-3-cyanoguanidine, 1-(4'-methoxybenzoyl)-3-cyanoguanidine, 1-(4'-methylsulfinylbenzoyl)-3-cyanoguanidine or 1-(4'-methylsulfonylbenzoyl)-3-cyanoguanidine may be substituted for the 1-(4'-methylthiobenzoyl)-3-cyanoguanidine in the above pharmaceutical composition.

EXAMPLE 5

A mixture of 500 parts of 1-(4'-methylthiobenzoyl)-3-cyanoguanidine, 60 parts maize starch and 20 parts of gum acacia is granulated with a sufficient quantity of water. The mass is passed through a 12-mesh screen and the granules are dried in a current of warm air. The dry granules are dried in a current of warm air. The dry granules are passed through a 16-mesh screen, mixed with 5 parts of magnesium stearate and compressed into tablet form suitable for oral administration.

Similarly, an equivalent amount of 1-(2'-methoxybenzoyl)-3-cyanoguanidine, 1-(3'-methoxybenzoyl)-3-cyanoguanidine, 1-(4'-methoxybenzoyl)-3-cyanoguanidine, 1-(4'-methylsulfinylbenzoyl)-3-cyanoguanidine or 1-(4'-methylsulfonylbenzoyl)-3-cyanoguanidine may be substituted for the 1-(4'-methylthiobenzoyl)-3-cyanoguanidine in the above pharmaceutical composition.

EXAMPLE 6

1. Tablets - 10,000 scored tablets for oral use, each containing 500 mg. of active ingredient are prepared from the following ingredients:

|  | G. |
|---|---|
| 1-(4'-methylthiobenzoyl)-3-cyanoguanidine | 5000 |
| Starch, U.S.P. | 350 |
| Talc, U.S.P. | 250 |
| Calcium stearate | 35 |

The powdered 1-(4'-methylthiobenzoyl)-3-cyanoguanidine is granulated with a 4% w./v. aqueous solution of methylcellulose U.S.P. (1,500 cps.). To the dried granules is added a mixture of the remainder of the ingredients and the final mixture compressed into tablets of proper weight.

2. Capsules - 10,000 two-piece hard gelatin capsules for oral use, each containing 250 mg. of 1-(4'-methylthiobenzoyl)-3-cyanoguanidine are prepared from the following ingredients:

|  | G. |
|---|---|
| 1-(4'-methylthiobenzoyl)-3-cyanoguanidine | 2500 |
| Lactose, U.S.P. | 1000 |
| Starch, U.S.P. | 300 |
| Talc, U.S.P. | 65 |
| Calcium stearate | 25 |

The powdered 1-(4'-methylthiobenzoyl)-3-cyanoguanidine is mixed with the starch-lactose mixture followed by the talc and calcium stearate. The final mixture is then encapsulated in the usual manner. Capsules containing 10, 25, 50, and 100 mg. of 1-(4'-methylthiobenzoyl)-3-cyanoguanidine are also prepared by substituting 100, 250, 500, and 1000 g. for 2,500 g. in the above formulation.

3. Soft elastic capsules - One-piece soft elastic capsules for oral use, each containing 200 mg of 1-(4'-methylthiobenzoyl)-3-cyanoguanidine are prepared in the usual manner by first dispersing the powdered active material in sufficient corn oil to render the material capsulatable.

4. Aqueous suspension - An aqueous suspension for oral use containing in each 5 ml., 1 gm. of 1-(4'-methylthiobenzoyl)-cyanoguanidine is prepared from the following ingredients:

| 1-(4'-methylthiobenzoyl)-3-cyanoguanidine | g. | 2000 |
|---|---|---|
| Methylparaben, U.S.P. | g. | 7.5 |
| Propylparaben, U.S.P. | g. | 2.5 |
| Saccharin sodium | g. | 12.5 |
| Glycerin | ml. | 3000 |
| Tragacanth powder | g. | 10 |
| Orange oil flavor | g. | 10 |
| F.D.& C. orange dye | g. | 7.5 |
| Deionized water, q.s. to 10 liters. | | |

Similarly, an equivalent amount of 1-(2'-methoxybenzoyl)-3-cyanoguanidine, 1-(3'-methoxybenzoyl)-3-cyanoguanidine, 1-(4'methoxybenzoyl)-3-cyanoguanidine, 1-(4'-methylsulfinylbenzoyl)-3-cyanoguanidine or 1-(4'-methylsulfonylbenzoyl)-3-cyanoguanidine may be substituted for the 1-(4'-methylthiobenzoyl)-3-

What is claimed is:

1. A compound of the formula:

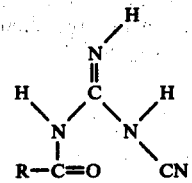

wherein
R is $C_{1-5}$alkylthiophenyl, $C_{1-5}$alkylsulfinylphenyl or $C_{1-5}$alkylsulfonylphenyl.

2. The compound of claim 1 wherein
R is methylthiophenyl, methylsulfinylphenyl of methylsulfonylphenyl.

3. 1-(4'-Methylthiobenzoyl)-3-cyanoguanidine according to claim 2.

4. A pharmaceutical composition useful for treating inflammation and rheumatoid arthritis comprising a non-toxic pharmaceutically acceptable carrier and a therapeutically effective amount of a compound of the formula:

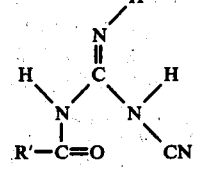

wherein
R' is $C_{1-5}$alkoxyphenyl, $C_{1-5}$alkylthiophenyl, $C_{1-5}$alkylsulfinylphenyl or $C_{1-5}$alkylsulfonylphenyl.

5. A method of treating rheumatoid arthritis which comprises administering to a patient a therapeutically effective amount of a compound of the formula:

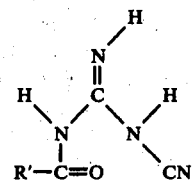

wherein
R' is $C_{1-5}$alkoxyphenyl, $C_{1-5}$alkylthiophenyl, $C_{1-5}$alkylsulfinylphenyl or $C_{1-5}$alkylsulfonylphenyl.

* * * * *